United States Patent [19]

Apontoweil et al.

[11] Patent Number: 4,500,638

[45] Date of Patent: Feb. 19, 1985

[54] INFECTIOUS BRONCHITIS VIRUS STRAIN

[75] Inventors: Peter Apontoweil, Leersum; Manfred M. Krasselt, De Bilt, both of Netherlands

[73] Assignee: Gist-Brocades N.V., Delft, Netherlands

[21] Appl. No.: 437,517

[22] Filed: Oct. 29, 1982

Related U.S. Application Data

[62] Division of Ser. No. 209,583, Nov. 24, 1980, Pat. No. 4,357,320.

[30] Foreign Application Priority Data

Nov. 30, 1979 [NL] Netherlands ......................... 7908687
Sep. 9, 1980 [NL] Netherlands ......................... 8005063

[51] Int. Cl.$^3$ ............................................... C12N 7/00
[52] U.S. Cl. ....................................... 435/235; 424/89
[58] Field of Search ....................... 435/235, 236, 237; 424/89

[56] References Cited

PUBLICATIONS

Darbyshire et al., Archives of virology, 61: 227–238 (1979), "Taxonomic Studies on Strains of Avian Infectious Bronchitis Virus Using Neutralization Tests in Trachial Organ Cultures".

Winterfield et al., Am. J. Vet. Res., 36: 524–526, Apr., 1975, "Potential for Polyvalent Infectious Bronchitis Vaccines".

Winterfield, Avian Dis., 12: 577–584 (1968), "Respiratory Signs, Immunity Response, and Interference from Vaccination with Monovalent and Multivalent Infectious Bronchitis Vaccines".

Primary Examiner—Sam Rosen
Attorney, Agent, or Firm—Charles A. Muserlian

[57] ABSTRACT

Infectious bronchitis (IB) vaccines for poultry derived from at least one novel virus strain of novel infectious bronchitis serotypes, selected from the group consisting of culture Nos. CNCTC A 07/80, CNCTC A 08/80, CNCTC A 09/80, CNCTC A 010/80, CNCTC A 011/80, CNCTC A 013/80, CNCTC A 014/80, CNCTC A 015/80 and CNCTC A 016/80 deposited at the Czechoslovak National Collection of Type Cultures of the Institute of Hygiene and Epidemiology in Prague, Czechoslovakia and the novel viruses per se, combined virus vaccines and a novel method of protecting poultry from infectious bronchitis.

4 Claims, No Drawings

INFECTIOUS BRONCHITIS VIRUS STRAIN

This application is a divisional of co-pending U.S. patent application Ser. No. 209,583, filed Nov. 24, 1980, now U.S. Pat. No. 4,357,320.

STATE OF THE ART

The application of live infectious bronchitis vaccines for poultry has been known for many years and infectious bronchitis is an important affection of the respiratory system kidneys and oviduct of poultry caused by a corona virus. The poultry is severely affected by epizootics of this disease. Infectious bronchitis still causes a large mortality, especially with young poultry. Besides the mortality and more or less strong respiratory symptoms, lesions to the oviducts occur and as a result thereof, egg production drops caused by an IB infection occur. Moreover, infections with IB virus may stimulate latent virus or bacterial infections and may give rise in this way to severe economical losses, especially in the broiler field.

For combatting infectious bronchitis, vaccines derived from inactivated virus as well as those derived from live virus are used, but it was found that a loss of immunogenic properties occurred after inactivation of these vaccines with e.g. formaline and ultra violet light (M. S. Hofstad, Diseases of Poultry, Biester and Schwarte, Iowa State University Press, Ames. (1965), 615). Since normal, sound chickens are often killed by vaccination with a live, non or less attenuated virus vaccine, whereby an especial danger existed for animals less than 2 or 3 weeks old or for chickens shortly before the start of or during laying, people skilled in this art have a clear preference for the application of dead vaccines or of live vaccines with which was tried to increase the harmlessness of such vaccines by means of attenuation of the original IB field virus isolated.

For example, the H-strain which is presently used on a world wide scale due to its broad immunization spectre was isolated and attenuated by Bijlenga et al and is disclosed in Tijdschrift Diergeneesk Vol 81, page 43, "Infectious bronchitis in chicks in the Netherlands" (1956), Tijdschr. Diergeneesk., Vol. 85, page 320 (1960), Tijdschr. Diergeneesk., Vol. 85, page 279 (1960) and Tijdschr. Diergeneesk., Vol. 85, page 398 (1960). For such modified vaccines, viruses having undergone 25 or more embryo passages to reduce their pathogenicity and their disseminating ability have been used up to now, such as e.g. the Massachusetts type and more particularly the IBV W 48, M41, 82828 or the H52 H120 strains thereof (the last two having been passaged 52 and 120 times, respectively, on embryonated chicken eggs), a Connecticut isolate, e.g. A 5968 or the Beaudette IBV type (IBV-42).

Although the use of vaccines of these modified strains has presently appeared to be safe and effective, these vaccines have appeared to be still unable to prevent outbreaks of infectious bronchitis in a sufficient way under certain conditions as appears from Avian diseases Vol. 20, No. 1, pages 42 and 177 and Avian Diseases Vol. 19, No. 2, pages 323 and 583. This shortcoming of the present IB vaccines is attributed to antigenic variations of the virus occurring to an important degree as appears e.g. from Archiv fur die Gesamte Virusforschung 34, page 32 (1971) and Cunningham C. H., Develop. Biol. Standard 33, 311 (1976).

Efforts were made therefore to obtain an adequate vaccination of poultry by preparation and application of combined vaccines derived from several IBV strains of different serotypes. However, hereby a clearly encountered difficulty appeared to form the decrease of immunogenic properties of the respective starting viruses caused by mutual interaction as appears from Am. J. Vet. Res. Vol. 36, pages 4, 524 nand 525 (1965) and Avian Diseases Vol. 12, page 577 (1968). Therefore, there still exists a great need for IB vaccines with adequate immunizing properties. It will be appreciated that the desired improvement of these vaccines is still severely hampered due to changing immunogenic and other properties of the presently available IB virsuses after a large number of passages in embryonated chicken eggs, the appearance of new serotype and the lack of sufficiently effectively applicable serological and immunological test procedures respectively. In this connection, reference may be made to Avian Diseases, Vol;. 19, pages 2, 323 and 324 (1975).

OBJECTS OF THE INVENTION

It is an object of the invention to provide novel man-made virus strains of novel infectious bronchitis virus serotypes and to novel vaccines for poultry derived from the said viruses.

It is another object of the invention to provide novel processes for the preparation of infectious bronchitis vaccines for poultry and novel combined vaccines.

It is a further object of the invention to provide a novel method of protecting poultry from infectious bronchitis.

These and other objects and advantages of the invention will become obvious from the following detailed description.

THE INVENTION

The novel viruses of the invention are selected from the group consisting of culture Nos. CNCTC A 07/80, CNCTC A 08/80, CNCTC A 09/80, CNCTC A 010/80, CNCTC A 011/80, CNCTC A 013/80, CNCTC A 014/80, CNCTC A 015/80 and CNCTC A 016/80 deposited at the Czechoslovak National Collection of Type Cultures of the Institute of Hygiene and Epidemiology in Prague, Czechoslovakia. The said viruses were also deposited at the Collection Nationale de Cultures de Microorganismes d'Institut Pasteur, Paris under the respective numbers according to the following Table in which the assignees internal references are also given.

TABLE I

| Internal No. | Czech. No. | date of deposit | Paris No. | date of deposit |
|---|---|---|---|---|
| Utrecht 101 | A 07/80 | 3-6-80 | I-111 | 11-14-79 |
| Utrecht 102 | A 08/80 | 3-6-80 | I-112 | 11-14-79 |
| Drente 201 | A 09/80 | 3-6-80 | I-113 | 11-14-79 |
| Limburg 501 | A 010/80 | 3-6-80 | I-109 | 11-14-79 |
| Limburg 502 | A 011/80 | 3-6-80 | I-110 | 11-14-79 |
| Brabant 801 | A 016/80 | 9-9-80 | I-132 | 10-3-80 |
| Limburg 536 | A 014/80 | 9-9-80 | I-134 | 10-3-80 |
| Overijssel 728 | A 015/80 | 9-9-80 | I-135 | 10-3-80 |
| Utrecht 121 | A 013/80 | 9-9-80 | I-333 | 10-3-80 |

As a result of extensive research and experimentation, the novel IB viruses were surprisingly obtained and can be regarded as deviating from the up to now most frequently applied IB viruses of the H type such as (IB H120 and IB H52) in cross neutralization tests (virus neutralization tests) according to e.g. the method described in American Association of Avian Pathologists, "Isolation and Identification of Avian Pathogens", page 184 (1975), with the understanding that antisera diluted in a ratio of 1:5 are used, and in challenge experiments with subsequent virus reisolation tests. In other words, with an inoculation with a virus of the H-type, the concerned animals were not protected against virus replication in the mucosa of the respiratory system after a challenge with the before mentioned derivating novel IB viruses.

Humoral antibodies against the IB H strain equally appeared not to be able to neutralize significant amounts of IB virus of the mentioned deviating types. Of special importance for the practice is that these novel IB viruses cause respiratory symptoms with animals showing high antibody titers against the IB H strain and with still laying animals, egg production drops.

The viruses were isolated by means of the trachea swab method with flocks of laying chickens which had been vaccinated two and three times repsectively with IB H120 and IB H52 vaccine and which showed high humoral antibody titers as to the Massachusetts type of the IB virus at the beginning of the occurrence of respiratory symptoms and egg production drops and with broilers which showed in the second half of the cram period respiratory symptoms after previous vaccinations with IB vaccine of the H120 type, whereby both types of animals found themselves at the moment of isolation in districts which have been indicated in the hereinbefore used internal notations.

There was now found that by attenuation to SPFchicken embryos, the isolated virus strains have lost their pathogenicity for SPF chickens to a major degree in spite of the fact that their immunizing ability has remained still present. For example, the virus strain with internal notation IBV Utrecht 101 showed these before mentioned characteristics after 85 SPF type I chicken embryo passages and the virus-strain IBV Limburg 536 showed these characteristics after 56 SPF type I chicken embryo passages.

There was surprisingly found during a comparison test using conventional H120 or H52 vaccines that the protection against IB viruses of the Massachusetts type, measured by the amount of virus neutralizing antibodies, had not been diminished to a significant degree, if a H-type vaccine combined with e.g. the novel IBV isolate Utrecht 101 was administered instead of the H-type vaccine. During this experimentation, one started from intranasal application of the concerning vaccines.

For instance, the following neutralization indices were determined 4 weeks after administration of the respective vaccines and vaccine combinations.

TABLE 2

Immunizing ability of different vaccines measured on the humoral immune response (neutralization index).

| Vaccine | test virus N.I.H. (B222) | IBV Utrecht 101 | IBV Limburg 536 |
|---|---|---|---|
| 1. H120 | 6.5 | 1.7 | 0.8 |
| 2. IBV Utrecht 101 (82nd egg passage) | 2.1 | 6.8 | N.D. |
| 3. H120 + IBV Utrecht 101 | 6.2 | 6.5 | N.D. |
| 4. IBV Limburg 536 (53rd egg passage) | 0.9 | N.D. | 5.8 |
| 5. H120 + IBV Limburg 536 | 6.7 | N.D. | 5.7 |

In addition to the immuno response after administration of different vaccines and vaccine combinations respectively, the resistance against virus replication and persistence was also determined in and on the mucosa of the trachea determined by the virus reisolation technique described in "Specifications for the production and control of avian live virus vaccines" of the Ministry of Agriculture, Fisheries and Food of the United Kingdom Central Veterinary Laboratory of Biological Products and Standards Department, New Haw, Weybridge, Surrey KT 153 NB, 2nd Edition (1977), page 12.

Cross neutralization tests in SPF chicken embryos and cross infection tests on SPF chickens were carried out according to Tables 3 and 4.

TABLE 3

Cross neutralization test in SPF chicken embryos

| Antiserum against virus type | virus isolate | | | |
|---|---|---|---|---|
|  | H | Utrecht 101 | Overijssel 728 | Limburg 536 |
| H | $\geq 7.2$ | neg. | neg. | neg. |
| Utrecht 101 | neg. | 5.3 | neg. | neg. |
| Overijssel 728 | neg. | neg. | 5.8 | neg. N.I. ($10^x$) |
| Limburg 536 | neg. | neg. | neg. | $\geq 6.2$ |

In this connection with the expression "neg" means that no significant positive neutralization index (N.I.), i.e. N.I. $\leq 10^{2.0}$ was obtained.

TABLE 4

Cross challenge tests carried out on SPF chickens; results of virus reisolation tests

| Vaccine virus | challenge virus | | | |
|---|---|---|---|---|
|  | "VOET" type Massachusetts | Utrecht 101 | Overijssel 728 | Limburg 536 |
| H 120th egg-passage | neg. | + | + | + |
| Utrecht 101 50th egg-passage | + | neg. | + | + |
| Overijssel 728 100th egg-passage | + | + | neg. | + |
| Limburg 536 80th egg-passage | + | + | + | neg. |

The term "neg." means in this connection that none of the SPF eggs, injected with the trachea swab material showed symptoms which could be attributed to an infection with IB virus.

From the results of Tables 3 and 4 (neutralization and cross challenge tests), it appears that the four serotypes of the IB virus, namely those of the H-, Utrecht 101, Overijssel 728 and Limburg 536 types, not only differ antigenitically from each other, but additionally, having in mind the results of the infection experiments with additional virus reisolation, show attractive immunogenic properties as to the homolog virus. Field experiments showed that in sera of broilers, reproduction chickens and laying hens, antibodies were frequently occurring against the virus types Utrecht 101, Limburg 536 and Overijssel 728.

It will be appreciated therefore that the novel IB virus types are not only differing antigenitically in a significant degree from the up to now usually applied H-virus, but also show significantly different properties as to each other. For example, the isolated virus strains could be additionally characterized by the following tests.

Treatment of the infectious amnoin allantoic fluid obtained by cultivation of original virus containing samples from infected homogenized organ and trachea swab material in the allantoic hole of 10 day old prebrooded SPF eggs with chloroform according to Mayr et al, Virologische Arbeitsmethoden G. Fisher Verlag, Jena, 1977, page 285 resulted, in comparison with the non treated material, in a reduction of the repeatedly measured virus content from $10^{7.5}$ to $10^{1.5}$ $EID_{50}$. This experience may point to the presence of a virus agent, which contains in its envelope a lipid which is necessary for the infectivity. The infectious amnion-allantoic fluid caused no agglutination with erythrocytes derived from SPF chickens.

Addition of 5-fluordesoxyuridine (FUDR) to the culture medium of chicken kidney cell cultures, serving as a replication of the agent, did not influence the intracellular synthesis of the virus agent to a significant degree. The $EID_{50}$ content of the cell material and culture medium appeared the reside on comparable levels 2,4 and 7 days after the inoculation of the virus agent, i.e. the nucleic acid to be replicated belonged to the group of the ribonucleic acid.

Examination with electron microscope showed that the virus agent present in the amnion allantoic fluid which was harvested within 30 hours after the artificial infection possessed a diameter of about 100 nm. About 15 nm long projections were present on the surface of this virus and the virus had the size and shape of a corona virus to which also the aviar bronchitis viruses belong.

It will be appreciated that the properties of the novel virus types as described hereinbefore make the novel virus strains especially suitable for the preparation of inactivated as well as live poultry vaccines for a more efficient protection against infectious bronchitis, especially in areas or countries wherein the described deviating sterotypes of the present invention occur besides the IB viruses of the so called H-type. More particularly, virus strains of the serotypes of the hereinbefore mentioned novel virus strains may successfully be used for the preparation of mixed live and inactivated vaccines derived from one or more virus strains of the H-type as well as from one or more of the novel IB virus strains.

The novel IBV vaccines of the present invention may be obtained be propagation of one or more novel virus strains by methods known in principle in the art and optionally followed by inactivation by methods known in the art in principle. For instance, the virus may be propagated in fertilized SPF chicken eggs or in suitable cell cultures such as chicken kidney cell cultures. However, with such a process, the antigenic properties have to be checked to see that they do not change in such a way that the concerned viruses are no more, or to a much lesser degree, suitable for vaccination purposes. Then, the cultivated virus material is collected and purified and finally one or more stabilizers and possibly antibiotics such as sodium penicillin G, streptomycin or natamycin may be added and the mixture is lyophilized.

More particularly, the concerned seed virus is inoculated under sterile conditions in the allantoic hole in 10 to 11 days prebrooded chicken eggs of type I SPF. After incubation for 28 to 34 hours at 37° C., the amnion-allantoic fluid of the then still living and of the specifically died (i.e. after 24 hours after the seed virus inoculation) embryos is harvested, purified and lyophilized after optional addition of stabilizers and/or antibiotics. According to this process, single vaccines can be prepared which contain the virus, after lyophilizing, in an amount of $\geq 10^{4.0}$ $EID_{50}$ per dose, while e.g. so prepared combined vaccines of a novel virus strain and a known H-strain or of more novel virus strains showed a virus content of $\geq 2 \times 10^{4.0}$ $EID_{50}$ per dose and preferably a content of each of the virus components of $\geq 10^{4.0}$ $EID_{50}$ per dose.

It will be appreciated that the present invention also relates to novel, inactivated as well as live IBV vaccines which have been derived from at least one of the novel IB virus strains and to the use of such vaccines. Preferably live vaccines derived from one of the viruses of the H-type and one or more of the novel viruses are used. More preferably, live vaccines derived from H120 or H52 virus strain and from one or more IB viruses selected from the group consisting of Utrecht 101, Limburg 536 and Overijssel 728 are used. The vaccines may also be used with young animals and, more preferably, the broilers.

the vaccines may be administered by the so called eye drop or nose drop, the drinking-water or spray methods for live vaccines. Vaccination with novel live vaccines of the present invention is preferably effected on poultry of an age of 1 day to 18 weeks. The novel inactivated vaccines are subcutaneously or intramuscularly administered to animals. It will be appreciated that also combined live or inactivated vaccines derived from at least one of the novel IB virus types and one or more completely other diseases causing virus types such as e.g. Newcastle disease virus, adeno- or reo virus form a feature of the present invention too, preferably in a volume ratio of harvest liquids of about 3 parts IBV liquid to 2 parts liquid containing the other different virus.

For the preparation of inactivated IBV vaccines of the present invention, there may be started from e.g. an amnion-allantoic fluid to which a suitable carrier is added after inactivation by methods known in the art, e.g. by means of $\beta$-propiolactone or formaline. Preferably, the virus liquid of a suitable titer is processessed to an oil in water emulsion vaccine derived from a mineral or vegetable oil and one or more emulsifiers such as nonionic, surface-active compounds derived from alkylene oxide and/or hexahydric alcohols and/or higher natural fatty acids ($C_{10}$-$C_{20}$) such as esters or estereth- ers. Examples of the last mentioned emulsifiers are mannide monooleate [Span 80, Arlacel 80, Arlacel A] and polyoxyethlyene (20) sorbitan monooleate [e.g. Tween 80]. The volume ratio between the aqueous phase (virus fluid) and the oily phase may vary from 3:7 to 1:1 and lies preferably in a ratio of about 7:13.

In the following examples there are described several preferred embodiments to illustrate the invention. However, it is to be understood that the invention is not intended to be limited to the specific embodiments.

EXAMPLE 1

Preparation of IB virus vaccine of the strain Utrecht 101

A. Cultivation of virus

Type I SPF chicken eggs which were prebrooded for 10 to 11 days were inoculated with $10^{3.0}$ to $10^{4.0}$ $EID_{50}$ IBV Utrecht 101 seed virus (0.2 ml per egg) in the allantoic hole. The eggs were inspected for the first time 20 to 24 hours after the virus inoculation and all aspecific died embryos were removed. After an incubation period of a total of 28 hours at +37° C., the amnion allantoic fluid (AAF) was harvested.

B. Treatment of virus suspension

After purification of the AAF by centrifugation at 2000 r.p.m. in a cooling centrifuge and/or filtration, $5 \times 10^5$ units of sodium penicillin G and 800 mg of streptomycin per liter were added to this AAF. The virus material was subsequently stabilized by addition of at least 3% by weight of albumin and/or mannitol. The stabilized bulk virus material was frozen to at least $-35°$ C. and stored at that temperature until the further processing phase.

Samples of this material were mean while tested for their virus content by means of the $EID_{50}$ (Egg Infection Dose 50%) assay method. After the test results were available, the virus material was defrosted again and filled out into lyophilization flasks. The virus content (volume) was adjusted so that at the end of the subsequent lyophilization there was still at least $10^{4.5}$ $EID_{50}$ of the concerned virus per dose present in the vaccine. The flasks were sealed under vacuo at the end of the lyophilization.

With the preparation of a multivalent (mixed) vaccine, care had to be taken so that the minimal virus contents for all virus components were reached.

EXAMPLE 2

Preparation of IB virus vaccine of the strain Limburg 536

A. Cultivation of virus

Type I SPF chicken eggs which were prebrooded for 10 to 11 days were inoculated with $10^{3.0}$ to $10^{4.0}$ $EID_{50}$ IBV Limburg 536 seed virus (0.2 ml per egg) into the allantoic hole. The eggs were inspected for the first time 20 to 24 hours after the virus inoculation and all aspecifically died embryos were removed. After an incubation period of a total of 32 hours at +37° C., the AAF was harvested.

B. Treatment of the virus suspension

After purification of the AAF by centrifugation at 2000 r.p.m. in a cooling centrifuge and/or filtration, $6 \times 10^5$ units of sodium penicillin G and 900 mg of streptomycin per liter were added to this AAF. The virus material was subsequently stabilized by addition of about 5% by weight of albumin and/or mannitol. As albumin e.g. bovine albumin was used. The stabilized bulk virus material was subsequently frozen to a least $-35°$ C. and kept at such temperature until the further processing phase.

Meanwhile, samples of this material were tested for their virus content by the $EID_{50}$ (Egg Infectious Dose 50%) assay method and the virus material was defrosted again after the test results were available and filled into lyophilization flasks. The virus content (volume) was adjusted so that at the end of the lyophilization process, at least $10^{4.5}$ $EID_{50}$ of the concerned virus per dose was present in the vaccine. The flasks were sealed under vacuo at the end of the lyophilization.

During the preparation of multivalent (mixed) vaccine, care had to be taken that the minimum virus content for all virus components was reached.

EXAMPLE 3

Preparation of IB virus vaccine of the strain Overijssel 728

A. Cultivation of virus

Type I SPF chicken eggs which were prebrooded for 10 to 11 days were inoculated with $10^{3.0}$ to $10^{4.0}$ $EID_{50}$ IBV Overijssel.728 seed virus (0.2 ml per egg). The eggs were inspected for the first time 20 to 24 hours after the virus inoculation and all aspecifically died embryos were removed. After an incubation period of a total of 32 hours at +37° C., the AAF was harvested.

B. Treatment of the virus suspension

After purification of the AAf by centrifugation at 2000 r.p.m. in a cooling centrifuge and/or filtration, $8\times10^5$ units of sodium penicillin G and 1100 mg of streptomycin per liter were added to the AAF. The virus material was subsequently stabilized by the addition of about 7% by weight of albumin and/or mannitol. The stabilized bulk virus material was subsequently frozen to at least −35° C. and kept at this temperature until the further processing phase.

Meanwhile, samples of this material were tested for their virus content by the $EID_{50}$ assay method. The virus material was defrosted again and filled into lyophilization flasks after the test results were available. The virus content (volume) was adjusted so that at the end of the lyophilization process, at least $10^{4.5}$ $EID_{50}$ of the concerned virus per dose was present in the vaccine. The flasks were sealed under vacuo at the end of the lyophilization.

During the preparation of multivalent (mixed) vaccine, care had to be taken that the minimum virus content for all virus components was reached.

EXAMPLE 4

Preparation of a combined IB-virus vaccine of the strains Utrecht 101, Limburg 536 and Overijssel 728

A. Cultivation of virus

Type I SPF chicken eggs which were prebrooded for 10 to 11 days were inoculated with $10^{3.0}$ to $10^{4.0}$ $EID_{50}$ IBV Utrecht 101, Limburg 536 and Overijssel 728 seed virus (a total of 0.2 ml per egg) into the allantoic hole. The eggs were inspected for the first time 20 to 24 hours after from the virus inoculation and all aspecifically died embryos were removed. After an incubation period of a total of 32 hours at 37° C., the AAF was harvested.

B. Treatment of the virus suspension

After purification of the AAF by centrifugation at 2000 r.p.m. in a cooling centriuge and/or filtration, $8\times10^5$ units of sodium penicillin G and 1000 mg of streptomycin per liter were added to this AAF. The virus material was subsequently stabilized by addition of at least 3% by weight of albumin and/or mannitol. The stabilized bulk virus material was subsequently frozen to at least −35° C. and kept at this temperature until the further processing phase.

Meanwhile, samples of this material were tested for their virus content by the $EID_{50}$ assay method. The virus material was defrosted again and filled into lyophilization flasks after the test results were available. The virus content (volume) was adjusted so that at the end of the lyophilization process, at least $10^{4.5}$ $EID_{50}$ of the concerned virus per dose was present in the vaccine. The flasks were sealed under vacuo at the end of the lyophilization.

During the preparation of multivalent (mixed) vaccine. cary had to be taken that the minimum virus content for all virus components was reached.

EXAMPLE 5

Preparation of inactivated combined IB virus vaccine of the strains H 52, Utrecht 101, Limburg 536 and Overijssel 728

Using the procedure of Example 4 A., the virus was cultivated in SPF eggs and the obtained virus suspension was treated in a similar way as in Example 4. B. until the frozen phase was reached, but without the addition of antibiotics and stabilizers. The frozen AAF was defrosted and inactivated with 0.1% of β-propiolactone in a water bath for 90 minutes at 37° C. The virus suspension was kept overnight at ±4° C. and the inactivation was checked by inoculation of prebrooded embryonated SPF chicken eggs with the inactivated virus material and subsequent incubation.

The inactivated AAF was diluted if necessary with PBS +0.3% of formaline depending on the $EID_{50}$ of each virus type, determined in the non-inactivated AAF (at least $10^{7.0}$ for all virusstrains). To the virus suspension of the four strains, 3.5% of Tween 80 was added.

The inactivated virus suspension was mixed with an oily phase in the ratio of 6.5 parts of oil to 3.5 parts of virus fluid and emulsified so that the average particle size of the aqueous phase was about 0.5 μ. The emulsification was carried out with an Ultra Turrax homogenizer or by passing the starting mixture through a colloid mill. The oily phase had the following composition: 93.5% of Marcol 5 2 (white paraffinic Esso oil) and 6.5% Arlacel A, Arlacel 80 or Span 80 (mannide monooleate). The components of the oily phase were separately heated to 110° C. in an autoclave or the mixture was filtered under sterile conditions.

Various modifications of the compositions and methods of the invention may be made without departing from the spirit or scope thereof and it is to be understood that the invention is intended to be limited only as defined in the appended claims.

We claim:

1. A serotype virus strain of infectious bronchitis viruses selected from the group consisting of culture Nos. CNCTC A 07/80, CNCTC A 08/80, CNCTC A 09/80, CNCTC A 010/80, CNCTC A 011/80, CNCTC A 013/80, CNCTC A 014/80, CNCTC A 015/80 and CNCTC A 016/80 deposited at the Czechoslovak National Collection of Type Cultures with the Institute of Hygiene and Epidemiology in Prague, Czechoslovia.

2. A virus strain of claim 1 which is No. CNCTC A 07/80.

3. A virus strain of claim 1 which is No. CNCTC A 014/80.

4. A virus strain of claim 1 which is No. CNCTC A 015/80.

* * * * *